United States Patent
Griffith et al.

(10) Patent No.: US 8,744,781 B2
(45) Date of Patent: Jun. 3, 2014

(54) EDDY CURRENT METHOD FOR THE CHARACTERIZATION OF BROACHED TUBE SUPPORT PLATE BLOCKAGE

(71) Applicant: Areva NP Inc., Lynchburg, VA (US)

(72) Inventors: John C. Griffith, Lynchburg, VA (US); Joseph R. Wyatt, Lynchburg, VA (US); Mihai G. M. Pop, Alexandria, VA (US); Jeffrey M. Fleck, Forest, VA (US)

(73) Assignee: AREVA Inc., Lynchburg, VA (US)

( * ) Notice: Subject to any disclaimer, the term of this patent is extended or adjusted under 35 U.S.C. 154(b) by 0 days.

(21) Appl. No.: 13/970,819

(22) Filed: Aug. 20, 2013

(65) Prior Publication Data

US 2013/0338940 A1 Dec. 19, 2013

Related U.S. Application Data

(63) Continuation of application No. 12/702,142, filed on Feb. 8, 2010, now Pat. No. 8,527,216.

(60) Provisional application No. 61/271,691, filed on Jul. 24, 2009.

(51) Int. Cl.
*G01B 7/34* (2006.01)
*G01B 5/28* (2006.01)

(52) U.S. Cl.
USPC ............................................ 702/38; 324/222

(58) Field of Classification Search
USPC ............. 702/35, 38, 45, 46, 49, 157; 324/222
See application file for complete search history.

(56) References Cited

U.S. PATENT DOCUMENTS

| 4,763,274 A | 8/1988 | Junker et al. |
| 4,855,677 A | 8/1989 | Clark et al. |
| 5,025,215 A | 6/1991 | Pirl |
| 5,408,883 A | 4/1995 | Clark et al. |
| 7,405,558 B2 * | 7/2008 | Wyatt et al. .................. 324/228 |

FOREIGN PATENT DOCUMENTS

| KR | 10-2009-0070782 A | 7/2009 |
| WO | WO 2009/103922 | 8/2009 |

OTHER PUBLICATIONS

"Nuclear Services/Engineering Services: Steam Generator Quatrefoil Tube Support Plate Flow Blockage Assessment," Westinghouse Electric Company, Dec. 2008.*
Elder et al., "Role of NDE in Steam Generator Secondary Side Deposit Management," EPRI Steam Generator NDE Conference, Jul. 2001.
"Nuclear Services/Engineering Services: Steam Generator Asset Management Program," Westinghouse Electric Company, Oct. 2008.
Bodineau et al., "Tube support plate clogging up of French PWR steam generators," Eurosafe, 2008.
"Scale Profiling Enhances Steam Generator Performance," Westinghouse Worldview, Dec. 2004.

* cited by examiner

*Primary Examiner* — Manuel L Barbee
(74) *Attorney, Agent, or Firm* — Davidson, Davidson & Kappel, LLC

(57) ABSTRACT

A method for determining tube support plate blockage of a steam generator includes the following steps: measuring at least five different eddy current values per tube support intersection; calculating a nominal clean fit radius of flow hole; determining a center signal response; converting the center signal response to a deposit thickness; determine an edge reduction; converting the edge reduction to an edge thickness; calculating the resulting flow hole radius; verifying the reasonableness of the resulting flow hole radius; and determining a virtual calibration range.

19 Claims, 3 Drawing Sheets

EDDY CURRENT METHOD FOR THE CHARACTERIZATION OF BROACHED TUBE SUPPORT PLATE BLOCKAGE

Priority to U.S. patent application Ser. No. 12/702,142 filed Feb. 8, 2010, which claims priority to U.S. Provisional Patent Application Ser. No. 61/271,691 filed Jul. 24, 2009, is claimed, the entire disclosures of which are both hereby incorporated by reference herein.

The present invention relates generally to tube support plates of steam generators.

BACKGROUND

FIG. 1 shows a nuclear steam generator 52 which comprises a plurality of U-shaped tubes disposed within its shell to form tube bundles 50. Tube bundles 50 typically contain thousands of generator tubes. Tube sheets are provided for supporting the tubes at the ends opposite the U-shaped curvature. A primary fluid is heated in the reactor core through circulation and enters steam generator 52 through a primary inlet 54 fluid nozzle where it is distributed by upper tube sheet through the generator tubes and collected at the lower tube sheet. The fluid then flows through a primary fluid outlet 56 nozzle to the remainder of the reactor system. A feedwater stream is also introduced into steam generator 52 secondary side through a feedwater nozzle. The feedwater mixes, in steam generator 52, with water returning from moisture separators located above the tubes.

Tube bundles 50 also have a number of parallel tube support plates ("TSP") 58 that are arranged in tandem and spaced along the longitudinal length of bundles 50 through which heat exchange tubes pass and are supported against vibration. These TSP 58 can take many forms. The secondary water and generated steam flow through broached openings in TSP 58. Deposition forms from fine particles of magnetite at a relatively high temperature within the secondary water and also from ionic species which collect and concentrate when the secondary water boils and leaves as steam. Significant amounts of deposition are introduced in the feedwater. The deposition may be a combination of species depending on the chemistry of the feedwater. This deposition collects and builds up as sludge patches about broached openings of TSP 58, particularly on the free tube heat transfer surface which reduces the efficiency and the blockage within the support flow holes which acts as an impediment to the flow of feedwater and the water/steam mixture in the upper parts of the tube bundle as the water converts to steam.

The flow of boiling products, liquid or steam, through a TSP 58 intersections can be restricted by the presence of deposition on the open tube surface immediately adjacent to the lower and upper edges of TSP 58, deposition within the center of the TSP broached volume, or deposition growth from the TSP broached edges to the tube surface at the lower and upper openings to the TSP flow path. This later deposition growth condition at the lower edge of the support has been termed "webbing" since it resembles a densely woven spider web formation that has a thickness dimension considerably less than the surface area dimension. While "webbing" has been observed in a very small quantity of steam generators at the lower edge of the upper most TSP for a very small percentage of tube to tube support plate intersections, also called TSP flow region, this "webbing" formation does not represent the geometry of blockage for the remaining, larger population of TSP flow regions within the steam generator. FIG. 2 presents the configuration for a trefoil broached TSP design. The measurement and analysis methods for the invention are applicable to any broached TSP design.

Deposit formation produces an alteration of the eddy current response to the TSP, however the specific changes to the signal response have not been formally measured to determine the degree of flow restriction through the available volume of the TSP flow region.

A method to determine the effect of a measured pattern (collection or population) of flow restriction for a single or set of TSP on critical steam generator operational parameters has not been formulated. A current practice is to perform extensive visual examination of the TSP flow regions. This current practice requires unacceptable amounts of time and exposes personnel to large amounts of accumulated radioactive dose. If a steam generator does not provide access ports for visual inspection tooling between each pair of TSP, the visual examination is limited to accessible areas for the uppermost TSP. Even with full access to each TSP, only a small percentage of the total available TSP flow regions can be examined with the current visual inspection tooling technology. Consequently, a complete examination of the population of TSP flow regions is not possible and subsequent analysis of the effect of observed flow restriction of steam generator operational parameters would be subject to large uncertainties.

A proposed application of a flux leakage eddy current method presupposes the existence of a specific deposition formation "webbing" as the primary and substantial cause of TSP flow region clogging within the steam generator. While "webbing" has been observed in a small quantity of steam generators, in a small quantity of TSP flow regions at the uppermost TSP, "webbing" is not the primary deposition geometry for TSP flow regions in tube support plates below the uppermost TSP. EU Patent Application PCT/FR 2009/050232 for TSP clogging proposes the use of a bobbin coil method in addition to the flux leakage method to characterize the clogging within the TSP flow regions. This application does not provide a process to relate the collective measured results of the collective TSP flow regions to any of the critical operational parameters for the steam generator. While the proposed method may yield a relative pattern of clogging for a single or set of tube support plates, the application does not address any specific use of these results to ascertain the operational characteristics of the steam generator.

U.S. Pat. No. 7,405,558, incorporated by reference herein, teaches a method for the measurement of deposition on the open tube surfaces between pairs of TSP.

SUMMARY OF THE INVENTION

An object of the invention is to provide measured values from a bobbin eddy current examination of steam generator tubing to calculate the degree of flow restriction, "clogging," or "blockage," at each of the TSP flow regions, and subsequently, through the use of a blockage calibration method and a thermal/hydraulic model, determine one or more steam generator parameters such as the risk of pressure losses, water level changes, water level control stability, and undesired cross-flow patterns.

In the absence of a measured steam generator operation parameter to complete a virtual calibration, an iterative process is performed in the present invention to relate the population of flow area ratio results to possible steam generator operational parameter performance (i.e., a "what if" analysis).

The present invention provides a method which uses eddy current bobbin data to obtain multiple measures of the amount of deposition at the TSP flow region and a method to relate these measured values through a virtual calibration to one or more steam generator operational parameters to allow for risk assessment analysis of TSP blockage to the operational aspects of the steam generator. The method for determining tube support plate blockage of a steam generator includes the following steps: measuring at least five different eddy current values per tube support intersection; calculating a nominal clean fit radius of flow hole; determining a center signal response; converting the center signal response to a deposit thickness; determining an edge reduction; converting the edge reduction to an edge thickness; calculating the resulting flow hole radius; verifying the reasonableness of the resulting flow hole radius; and determining a virtual calibration range.

The measured values from the standard bobbin eddy current examination are obtained in a method consistent with that presented in U.S. Pat. No. 7,405,558. While this existing patent directly addresses the measurement of deposition along the length of an open tube surface between two adjacent TSP, the present invention applies the measurement method disclosed therein to the portion of the tube that passes through the TSP. Since the tube support plate material conducts eddy currents, modifications to the existing measurement method for the open tube surface are necessary to extract the deposition signal response from the always present tube support plate signal response.

BRIEF DESCRIPTION OF THE DRAWINGS

The present invention will be described further with respect to an embodiment of the present invention using the figures, in which.

DETAILED DESCRIPTION

Bobbin coil eddy current data is used to make calibrated quantitative measurements of deposition around and within the support. A bobbin coil eddy current probe is used to sense changes in the quantity of material deposited in and around the support plate as the probe is drawn axially through the tube. Various alterations in the eddy current TSP signal response are detected during the analysis of the eddy current data for open tube surface deposition and tubing flaws. Five separate measurements to characterize the deposition in the TSP region may be performed. Although these measured values may be used to determine the deposit loading within each tube support intersection, a more appropriate use has been found to determine the flow restriction present at each tube support intersection and subsequently the collective effect of the flow restriction of the population of tube intersections on several operational concerns for the steam generator.

Figure 3:
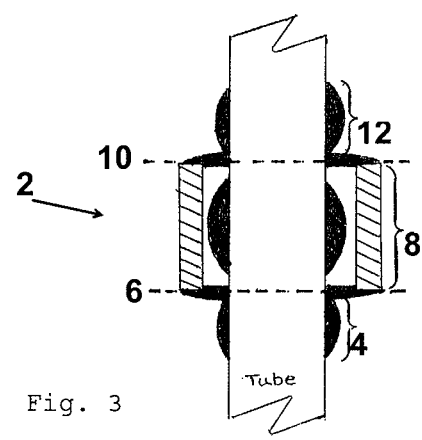
FIG. 3 shows the measurement locations of the tube.
Figure 4:
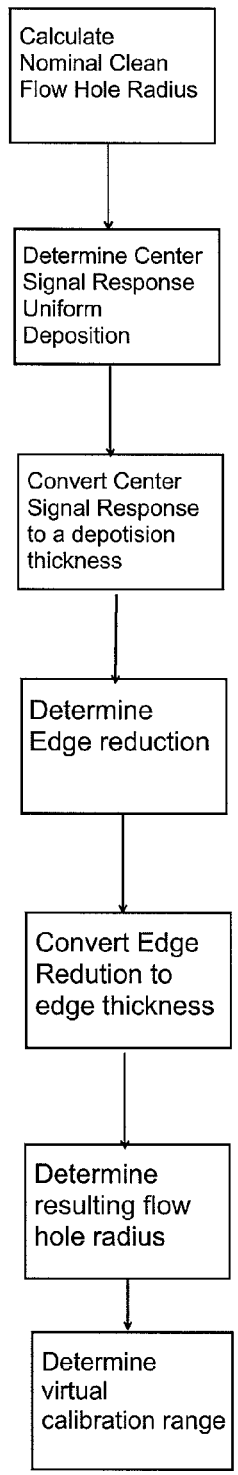
FIG. 4 is a flow chart showing the method of the present invention.

FIG. 3 shows a section of the tube support region 2. The five eddy current measurements are a Bin Below 4, Bin Above 12, TSP Center 8, TSP Lower 6 and TSP Upper 10. This set of measurements allow characterization of the deposition morphology at the TSP and a quantitative assessment of the blockage. Uniform deposition within the support is detected by TSP Center 8. Adjacent deposition above and below the TSP, Bin Above 12 and Bin Below 4, do not directly restrict flow within the limited flow hole area, but can restrict the flow coming into the flow hole or coming out the upper edge of the flow hole. TSP Lower 6 and TSP Upper 10 are within the TSP flow region and will show blockage within the flow hole.

Bin Below 4 is a deposit measurement for a given length along the free span immediately below tube support 2. Bin Below 4 is obtained to determine the presence of deposition adjacent to the lower edge of tube support 2. This measured value uses the same eddy current inspection frequency and datum (measurement reference) as an open tube surface deposit analysis. The deposition in these adjacent regions provides information on the flow restriction near the support.

Bin Above 12 is a deposit measurement taken for a given length along the free span immediately above tube support 2. Bin Above 12 is obtained to determine the presence of deposition adjacent to the upper edge of tube support 2. This measured value uses the same eddy current inspection frequency and datum (measurement reference) as the open tube surface deposit analysis.

TSP Center 8 is a tube support measurement taken anywhere within the tube support region relative to the open tube surface datum. TSP Center 8 measurement is obtained to determine the presence of deposition within the tube support region. This measured value uses the same eddy current inspection frequency and datum (measurement reference) as the open tube surface deposit analysis.

TSP Lower 6 is a measurement relative to the tube support center taken along the lower edge of the tube support signal response to determine the presence of "webbing." The webbing condition may occur in some generators at the lower edge of the upper most TSP. The magnitude of the TSP Lower 6 measurement versus TSP Center 8 measurement is more likely an indication of open tube surface deposition "spill over" into the lower half of the tube support region. A local reference baseline is defined at the center of each support. Therefore, these measurements establish their own relative baselines local to each support plate intersection. This measurement is obtained from the signal amplitude response of an eddy current inspection frequency between 30 kHz and 200 kHz.

TSP Upper 10 is a measurement relative to the TSP Center 8 taken along the upper edge of the tube support signal response to determine the presence of "spill over" from the open tube surface deposition above the tube support 2. A local reference baseline is defined at the center of each support. Therefore, these measurements establish their own relative baselines local to each support plate intersection. Both TSP Upper 10 and TSP Lower 6 This measurement is obtained from the signal amplitude response of an eddy current inspection frequency between 30 kHz and 200 kHz.

As discussed above, a combination of eddy current frequency data is used to obtain five specific measurements characterizing the deposition for each TSP flow region. Three of the five measurements are measured using the same eddy current inspection frequency as that used in an open tube surface deposit analysis, which is a frequency at or below 35 kHz. Two of the five measurements are measured using an eddy current frequency between 30 to 200 kHz.

One or more of the five measured values is used to calculate a flow area ratio (deposition blocked area divided by the original open area) for the TSP intersection and the collection of TSP intersections of these ratio values can be calibrated to determine the flow blockage for the entire tube support plate. The calibration process establishes a degree of restriction or clogging for one or more TSP intersections with the largest amount of flow area reduction. From this calibration, the remaining population of flow area ratios can be adjusted to yield a composite image of clogging for each TSP and consequently the clogging for the steam generator.

The process of determining the blockage value estimation for any given TSP flow region (the region where the tube passes through the support and thus the region within the broached flow holes) consists of using the five measured values defined above both individually and as aggregate measures. As an aggregate measure, the distribution of the values characterize a range of expected measurements for each parameter and thus the distributions of the TSP Center 8, Bin Above 12 and Bin Below 4 characterize the minimum and expected values for the uniform deposition around and within the flow hole. This distribution information is then used to better evaluate the uniform deposition within each support.

For example, since the support plate contributes some signal response which could be interpreted as deposition, the distribution minimum values are used to conservatively assign a "clean value baseline" for the support plate contribution and any value above that is assigned as a deposition signal. Although not exact, the use of the aggregate distribution values provides additional information which is otherwise unknown. The measurements of Bin Above 12 and Bin Below 4 are then used to provide additional correlation of the uniform deposition within the broached flow hole.

Figure 1:
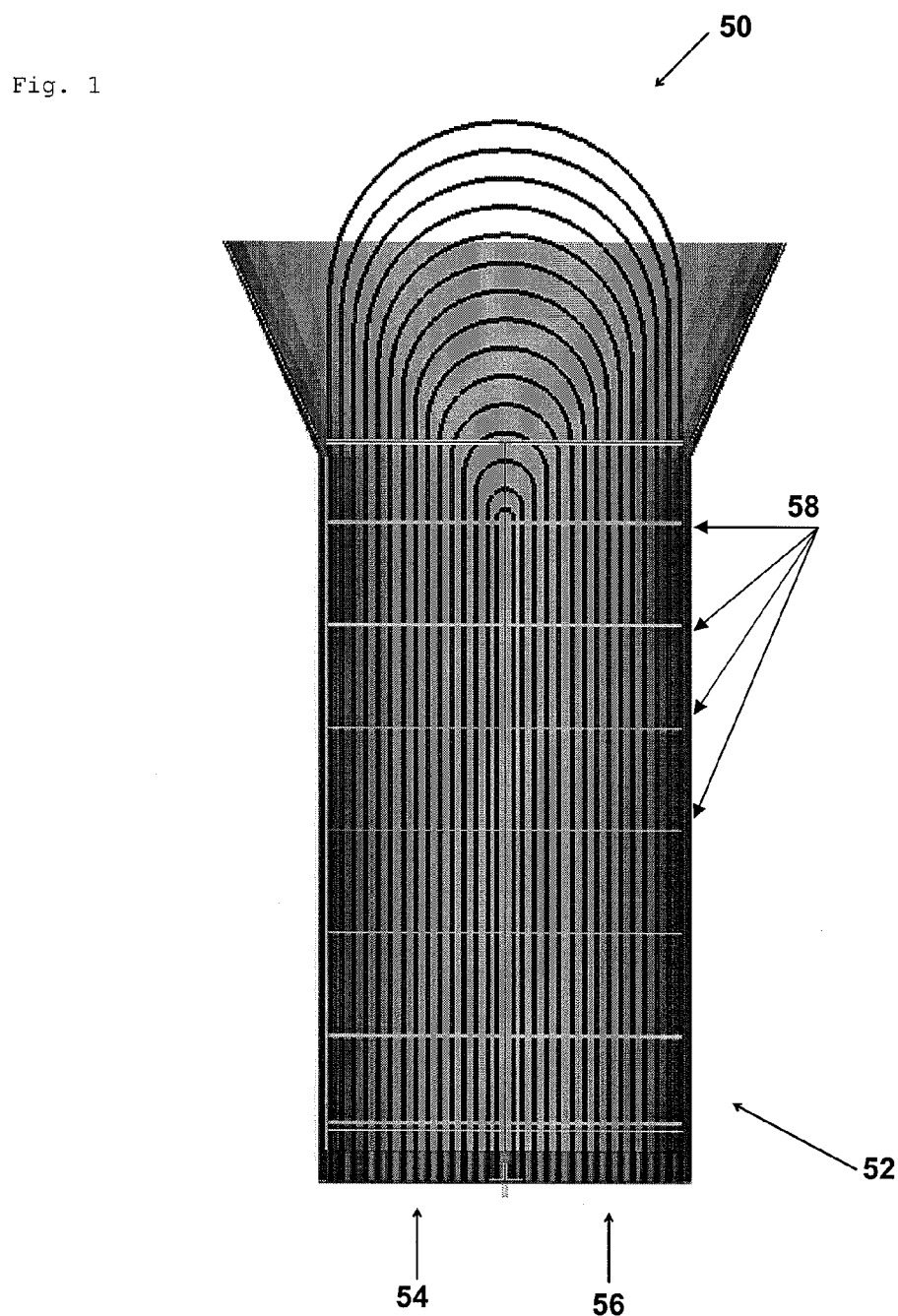
FIG. 1 shows a steam generator.
Figure 2:
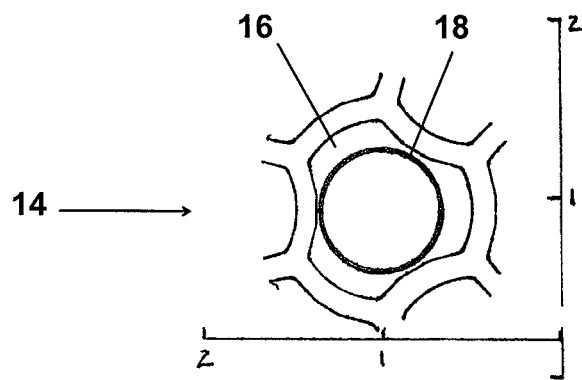
FIG. 2 shows a trefoil broached TSP configuration.

FIG. 2 shows a typical flow hole broach 14 adjacent to the tube outer diameter. Flow hole broach 14 consists of regions of open flow area 16 in which fluid flows and regions of near contact 18. The geometry of flow area 16 will vary based on the design of the support plate. FIG. 2 shows three flow areas 16 around the outer circumference of tube 18. The primary system fluid flows inside tube 18 and transfers heat to a secondary fluid, water and/or steam depending on the location in the steam generator, which travels through broached support flow holes 14. Uniform deposition within flow hole 14 reduces the available flow area. The uniform blockage occurs over a longer axial extent within the support broach and is well characterized by the lower frequency eddy current signal response. Empirical test data has also shown that many supports also have local deposit variations that are better detected by higher frequency eddy current due to their smaller axial extent. Thus the blockage may be roughly characterized by two components which are separately detected and characterized by different eddy current frequencies. The higher frequency data is indicated by the TSP Upper 10 and TSP Lower 6 measurements in the above discussion. Additional frequencies may also be used.

Due to the wide variation of signal responses in the TSP Upper 10 and TSP Lower 6 measurements, a definitive and deterministic calibration for this parameter is difficult to determine. However, the aggregate measurements are used to determine virtual calibration values. This process is somewhat analogous to a quantum system where the individual components are much more difficult to quantify, but the aggregate behavior is very clear.

By using the distributions and the virtual calibration value, the flow area reduction for each intersection may be calculated through an area calculation. It is assumed that each flow hole has an effective hydraulic radius and that the radius is reduced by both the uniform deposition value and by the shorter axial component. The resulting area change and calculation of the area ratio of clean/clogged is a geometric process.

Using this process, a unique area ratio is calculated for every TSP intersection (for each tube and each support plate). The average flow area is then used in conventional thermal hydraulic calculations known to those of ordinary skill in the art to determine the pressure drop across the entire tube bundle that would result for the steam generator operating conditions. This aggregate behavior of the steam generator is used to validate the virtual calibration of the flow areas.

As with any complex system, there are many sources of information that may be used to validate the virtual calibration. In the preferred embodiment, additional steam generator data may be used to adjust the virtual calibration value or to modify the area calculation (for example wide range level measurements, tube bundle pressure losses, etc.).

The preferred embodiment also extends to a probabilistic approach whereby the virtual calibration may be adjusted over a range of values to provide an expected or most likely condition or a worse case condition as needed for evaluating the effect of various blockage levels on generator performance.

For example, the TSP blockage (clogging) patterns in quantitative form can be applied as input to various thermo/hydraulic models, for example ATHOS, to study the effect of the TSP blockage on critical steam generator operational attributes such as pressure losses, water level (inventory) or cross flow velocities.

The following example provides a presently preferred embodiment of the method of the invention.

In a single broached support flow hole, the width of the hole is nominally 0.49" and the distance from the tube outer diameter to the flow hole outer diameter is 0.23". Thus the approximate area of a single flow hole is 0.112 square inches and the combination of four broached flow holes at one intersection of a quatrefoil broach design would have a combined area of 0.448 square inches. Considering a single flow hole with an area of 0.112 square inches, an equivalent radius of a round hole with the same area can be calculated. This equivalent radius is approximately 0.189 inches. Calculation of the hydraulic radius for the actual broached flow hole provides a very similar radius. Thus an equivalent radius of 0.189 inches is used. The Initial Radius (IR) of 0.189 inches is considered the nominal clean or unclogged flow hole equivalent radius.

Next, the deposit response within the center of the support, TSP Center 8, is measured. For example, assume a TSP Center 8 value of 1800 counts measured by the analysis program. All of the TSP Center 8 values have been measured within the generator and have the lower 95% confidence value for the distribution of TSP Center 8 values is 800 counts. This value of 800 counts is used as the clean TSP response with no deposit. Any TSP Center 8 value above the 800 counts will indicate some uniform deposition. It has been found that the Bin Above 12 and Bin Below 4 values are correlated with the uniform deposition within the support. These values are used to check or validate the selection of the 800 count clean baseline value. For the example TSP intersection with 1800 counts and a validated baseline of 800 counts, the signal due to uniform deposition, called Center Signal Response (CSR) is the 1000 counts.

Testing has shown that the uniform deposition within a support produces, as an example, a response of 200 counts per 0.001 inch thickness of deposit (CSR Calibration Signal Conversion Factor—in./counts). Thus for the case above, the detection of 1000 counts from deposition indicates a deposit thickness of 0.005 inches. This value would normally be a uniform deposit of 0.005 around the full circumference of the tube, however due to the presence of the support plate, the deposit responsible for the signal would have to reside in the three flow holes for a trefoil TSP or four flow holes for a quatrefoil TSP. A simplifying assumption is made to allow that the actual deposit thickness in each flow hole is 0.010 inches and is 0.000 inches otherwise. This means that the effective diameter of the flow hole would be reduced by 0.010 inches or the effective radius is reduced by 0.005 inches. For the example, the effective flow radius is reduced from 0.189 to 0.184 inches due to uniform deposition associated with the TSP Center signal response.

Few of the support flow holes will have a purely uniform deposition. While the lower frequency provides a good characterization of the uniform deposition (over larger axial extent) a higher frequency provides a more detailed profile of the deposition. The higher frequency provides more detail on the deposition profile and detects deposition buildup or webbing at either edge of the support flow hole. The TSP Upper 10 and TSP Lower 6 values measured at the higher frequency provide data on these variations. They are analyzed as changes or deltas relative to the value in the center of the support. For the current example, it is assumed that the TSP Upper 10 value is 20 counts and the TSP Lower 6 value is 370 counts measured at the higher frequency. This data indicates buildup on both the upper and lower edges and a simplifying assumption is applied to use only the maximum count value in the TSP Lower 6 flow hole reduction. The counts value selected for the Edge Signal Response (ESR).

Many different profiles have been observed in the TSP Upper 10 and TSP Lower 6 calculations, and the significance assigned to the TSP Lower 6 value of 370 counts is uncertain. However, many thousands of similar measurements on other intersections within the tube bundle may be used to determine the bounds on the significance of the measurements as a population. The determination of the bounds on the significance of a measurement based on a population of similar measurements using statistical methods is the virtual calibration. This process of virtual calibration is described below.

If a high frequency virtual calibration of 2 counts per 0.001 inch of edge deposition is assigned, then the support would have 0.185 mils of edge deposit and thus the resulting flow radius is 0.185 inch minus 0.185 inch or 0—the example flow hole would be found to be fully blocked. Applying the same virtual calibration to all 70000 intersections in the data set (the whole steam generator TSP intersections) will show whether the virtual calibration is a reasonable value, a conservative value or not possible. For example, if the virtual calibration value of 2 counts per 0.001 inch of edge deposit results in half of the intersections fully blocked, then this value is not reasonable.

Those of ordinary skill in the art know how to adjust the virtual calibration value (VCV in in/counts) to known conditions such as visual examination data or tube bundle pressure drops. By doing so the most likely range of the virtual calibration values can be determined. Thus the macro behavior of the set of all TSP intersection measurements may be used in validating the virtual calibration.

With the above, the formula to calculate the reduced radius for each TSP is:

Reduced Radius=Initial Radius−Uniform Reduction−
Edge reduction (1)

Or with the notations above:

Reduced Radius [in]=IR [in]−CSR [counts] CSR Calibration Signal Conversion Factor [in./counts]−
ESR [counts] VCV [in./counts] (2)

The flow hole reduction of area is defined per the invention:

Area Reduction=(Reduced Radius/IR)^2

The identical calculation applies for each of the four flow holes at a given intersection. The area ratio based on a single flow hole is duplicated for each of the four holes in the quatrefoil (or three holes in a trefoil broached support). In determining the flow area ratio from clean to clogged, all four flow holes may be considered. Since the above function will produce the same result for each flow hole within the support, the application to a single flow hole will produce the same result as applying the formula to all four holes.

The variability of the deposition profiles makes the development of a deterministic calibration standard or calibration process very costly and subject to significant error. However, by using the entire population of actual intersection measurement data, it is possible to determine the most likely range of the calibration. By applying the virtual calibration to all TSP intersection measurements, an area ratio is calculated for each intersection. The average area ratio for each support is used in standard thermal hydraulic calculations to determine the resulting pressure drop during operation. The virtual calibration can be validated or adjusted by comparing the calculated pressure drops to known operational conditions.

Using the above example, a virtual calibration for the edge factor of 2 would result in full blockage of the example TSP intersection. If the application of the virtual calibration to the full data set produces an average area ratio (area clogged divided by clean flow area) of 0.5 for the entire tube bundle and the resulting pressure drop was 300 psi, then it is clear that the factor of 2 is not valid. If the resulting pressure drop is 10 psi, then this value is clearly a reasonable calibration factor.

Using the calculation methods described above and the virtual calibration for the edge of TSP intersections of a given nuclear steam generator the results in Table 1 have been obtained for a preferred embodiment of the present invention:

TABLE 1

| | Calculated TSP Flow Hole Area Reductions | | | |
|---|---|---|---|---|
| TSP | Full TSP Average | Hot Leg Average | Cold Leg Average | Smallest Area |
| 1 | 0.813 | 0.819 | 0.808 | 0.339 |
| 2 | 0.779 | 0.798 | 0.760 | 0.290 |
| 3 | 0.836 | 0.836 | 0.835 | 0.195 |
| 4 | 0.808 | 0.785 | 0.832 | 0.082 |
| 5 | 0.818 | 0.795 | 0.841 | 0.079 |
| 6 | 0.796 | 0.769 | 0.822 | 0.265 |
| 7 | 0.739 | 0.707 | 0.770 | 0.175 |

In Table 1 values have been averaged for the more then 2000 TSP intersections of each of the 7 TSP of existing steam generators both on the hot portion of the steam generators called Hot Leg and the cold portion of the steam generators called Cold Leg.

The present invention provides a probabilistic method to develop a virtual calibration and through that determine valid TSP blockage information (verifiable through plant data such as pressure losses and level indications) even though a deterministic solution is not possible.

In the preceding specification, the invention has been described with reference to specific exemplary embodiments and examples thereof. It will, however, be evident that various modifications and changes may be made thereto without departing from the broader spirit and scope of the invention as set forth in the claims that follow. The specification and drawings are accordingly to be regarded in an illustrative manner rather than a restrictive sense.

What is claimed is:

1. A method for evaluating steam generator operational attributes comprising:
using eddy current measurements to determine blockage values of a plurality of tube support plate flow areas of a steam generator;

inputting the blockage values into a computer implemented thermo/hydraulic model, the input blockage values being probabilistically adjusted; and operating the computer implemented thermo/hydraulic model to estimate an effect of the blockage on critical steam generator operational attributes, wherein the blockage values are subject to a virtual calibration.

2. The method as recited in claim 1 wherein the critical steam generator operational attributes includes pressure losses, water level or cross flow velocities.

3. The method as recited in claim 1 wherein the using the eddy current measurements to determine the value for the blockage includes calculating a resulting flow hole radius at each of the tube support plate flow areas.

4. The method as recited in claim 1 wherein the blockage values are determined from a plurality of eddy current measurements at each of the tube support flow areas.

5. The method as recited in claim 4 wherein the plurality of eddy current measurements include measurements at a plurality of heights at each of the tube support flow areas.

6. The method as recited in claim 5 wherein the plurality of eddy current measurements includes measurements at at least one of above and below a tube support plate.

7. The method as recited in claim 5 wherein the plurality of eddy current measurements includes measurements at at least one of a top edge and a bottom edge of a tube support plate.

8. The method as recited in claim 4 wherein the plurality of eddy current measurements includes measurements detecting local deposit variations.

9. The method as recited in claim 8 wherein the plurality of eddy current measurements includes measurements detecting uniform deposition.

10. The method as recited in claim 1 wherein values from the virtual calibration are adjusted over a range of values to provide an expected condition or a worse case condition.

11. The method as recited in claim 1 further comprising measuring a plurality of eddy current values per tube support flow area.

12. The method as recited in claim 11 wherein the measuring is performed by an eddy current probe used to sense changes in the quantity of material deposited in and around the tube support plate flow areas.

13. The method as recited in claim 11 wherein the measuring a plurality of eddy current values per tube support flow area includes measuring at two different frequencies per tube support flow area.

14. A method of determining tube support plate blockage in a steam generator comprising:

using eddy current measurements to determine blockage values of a plurality of tube support plate flow areas of a steam generator;

characterizing a deposition morphology of each tube support flow area using the blockage values; and operating a computer implemented thermo/hydraulic model using the blockage values to estimate an effect of the blockage on critical steam generator operational attributes, wherein the blockage values are determined from a plurality of eddy current measurements at each of the tube support flow areas, wherein the plurality of eddy current measurements include measurements at a plurality of heights at each of the tube support flow areas.

15. The method as recited in claim 14 wherein the plurality of eddy current measurements include measurements at two different frequencies at each of the tube support flow areas.

16. A method for evaluating steam generator operational attributes comprising:

using eddy current measurements to determine blockage values of a plurality of tube support plate flow areas of a steam generator;

inputting the blockage values into a computer implemented thermo/hydraulic model, the input blockage values being probabilistically adjusted; and operating the computer implemented thermo/hydraulic model to estimate an effect of the blockage on critical steam generator operational attributes, wherein the using the eddy current measurements to determine the value for the blockage includes calculating a resulting flow hole radius at each of the tube support plate flow areas.

17. A method for evaluating steam generator operational attributes comprising:

measuring a plurality of eddy current values per tube support flow area;

using eddy current measurements to determine blockage values of a plurality of tube support plate flow areas of a steam generator;

inputting the blockage values into a computer implemented thermo/hydraulic model, the input blockage values being probabilistically adjusted; and operating the computer implemented thermo/hydraulic model to estimate an effect of the blockage on critical steam generator operational attributes, wherein the measuring a plurality of eddy current values per tube support flow area includes measuring at two different frequencies per tube support flow area.

18. A method of determining tube support plate blockage in a steam generator comprising:

using eddy current measurements to determine blockage values of a plurality of tube support plate flow areas of a steam generator;

characterizing a deposition morphology of each tube support flow area using the blockage values; and operating a computer implemented thermo/hydraulic model using the blockage values to estimate an effect of the blockage on critical steam generator operational attributes, wherein the blockage values are determined from a plurality of eddy current measurements at each of the tube support flow areas, wherein the plurality of eddy current measurements include measurements at two different frequencies at each of the tube support flow areas.

19. The method as recited in claim 18 wherein the plurality of eddy current measurements include measurements at a plurality of heights at each of the tube support flow areas.

* * * * *